(12) United States Patent
El-Aklouk et al.

(10) Patent No.: US 9,364,196 B2
(45) Date of Patent: Jun. 14, 2016

(54) METHOD AND APPARATUS FOR ULTRASONIC MEASUREMENT OF VOLUME OF BODILY STRUCTURES

(75) Inventors: Essa El-Aklouk, Thebarton (AU); John Brydon, Ovingham (AU)

(73) Assignee: Signostics Limited (AU)

( * ) Notice: Subject to any disclaimer, the term of this patent is extended or adjusted under 35 U.S.C. 154(b) by 0 days.

(21) Appl. No.: 13/133,654

(22) PCT Filed: Dec. 11, 2009

(86) PCT No.: PCT/AU2009/001608
§ 371 (c)(1),
(2), (4) Date: Jul. 5, 2011

(87) PCT Pub. No.: WO2010/066007
PCT Pub. Date: Jun. 17, 2010

(65) Prior Publication Data
US 2011/0263979 A1 Oct. 27, 2011

(30) Foreign Application Priority Data
Dec. 12, 2008 (AU) ................ 2008906408

(51) Int. Cl.
*A61B 8/00* (2006.01)
*A61B 8/14* (2006.01)
*G06T 7/60* (2006.01)
*G06T 7/00* (2006.01)

(52) U.S. Cl.
CPC . *A61B 8/14* (2013.01); *A61B 8/145* (2013.01); *G06T 7/602* (2013.01); *G06T 7/0085* (2013.01); *G06T 2207/10132* (2013.01); *G06T 2207/20182* (2013.01); *G06T 2207/20192* (2013.01); *G06T 2207/30084* (2013.01)

(58) Field of Classification Search
CPC ............... A61B 8/14; A61B 8/145; G06T 2207/10132; G06T 2207/30084; G06T 7/602
USPC ........................................... 600/438
See application file for complete search history.

(56) References Cited

U.S. PATENT DOCUMENTS

| 4,926,871 | A | | 5/1990 | Ganguly et al. | |
|---|---|---|---|---|---|
| 5,483,963 | A | * | 1/1996 | Butler et al. | 600/437 |
| 5,570,691 | A | * | 11/1996 | Wright et al. | 600/447 |

(Continued)

FOREIGN PATENT DOCUMENTS

JP 2004-275349 A 10/2004

OTHER PUBLICATIONS

Milkowski A., Yadong L., Becker D., Ishrak S. Speckle Reduction Imaging. [White Paper, GE Medical Systems, 2003].*

(Continued)

*Primary Examiner* — Jonathan Cwern
*Assistant Examiner* — Amelie R Gillman
(74) *Attorney, Agent, or Firm* — Craig A. Fieschko, Esq.; DeWitt Ross & Stevens, S.C.

(57) ABSTRACT

A method and apparatus for determining the volume of a bodily structure including the steps of acquiring at least two ultrasound images, estimating the location of the perimeter of a structure of interest as viewed in cross section in each said ultrasound image, calculating the cross sectional area of such structure as so viewed, and combining the perimeter and area information from the at least two images to calculate the volume of the structure.

9 Claims, 12 Drawing Sheets

(56) References Cited

U.S. PATENT DOCUMENTS

| | | |
|---|---|---|
| 5,964,710 A | 10/1999 | Ganguly et al. |
| 2004/0024315 A1* | 2/2004 | Chalana et al. ............... 600/443 |
| 2006/0084869 A1* | 4/2006 | Kim et al. .................... 600/437 |
| 2007/0066893 A1* | 3/2007 | Eriksen et al. ................ 600/436 |
| 2007/0083114 A1* | 4/2007 | Yang et al. ................... 600/437 |
| 2008/0232709 A1* | 9/2008 | Rahmes et al. ............... 382/260 |
| 2009/0112089 A1* | 4/2009 | Barnard et al. ............... 600/443 |
| 2010/0168576 A1* | 7/2010 | Poland et al. ................. 600/443 |

OTHER PUBLICATIONS

Song P, Tiew K, Lam Y, Koh L. A CMOS 3.4 mW 200 MHz Continuous-Time Delta-Sigma Modulator with 61.5 dB Dynamic Range and 5 MHz Bandwidth for Ultrasound Application. Circuits and Systems, Aug. 2007 (152-155).*

* cited by examiner

METHOD AND APPARATUS FOR ULTRASONIC MEASUREMENT OF VOLUME OF BODILY STRUCTURES

TECHNICAL FIELD

The present invention relates to a method and apparatus for determining the volume of an organ by use of ultrasound imaging. In particular the method and apparatus may be applicable to determination of the volume of a human or animal bladder.

BACKGROUND ART

At times it is clinically useful to know the area or spatial volume of a structure within the body. Examples are the cross section of the abdominal aorta and the volume of the bladder. Non-invasive bladder volume measurement techniques with ultrasound sonography have been described in the art. In principle, ultrasound scanning measures distance based on echo travel time. Early echo techniques used a single ultrasound transducer and echo presentation was recorded as echo amplitude versus depth. A method for determining bladder volume to determine residual urine volume based on distance measurement to the dorsal posterior bladder wall was described in the 1960's. The method was not adjusted to specific, filling dependent, measuring configurations.

A relation between the difference in echo travel time between echoes from the posterior an anterior bladder wall and the independently measured bladder volume was recognised. Volume measurement methods based on this observation have been described. The methods are exclusively based on bladder depth measurement. Since the bladder changes in shape when filling, a single distance measurement is not precise enough to predict the entire bladder volume. No filling dependent measurement configuration is used.

Diagnostic ultrasound is today well known for real-time cross-sectional imaging of human organs. For cross-sectional imaging the sound beam is swept electronically or mechanically through the cross section to be imaged. Echoes are presented as intensity modulated dots on a display, giving the well-known ultrasound sector scan display.

Bladder volume may be calculated based on bladder contours obtained in two orthogonal planes with a geometric assumption of bladder shape. For 3-dimensional or volumetric sonography the sound beam has to be swept through the entire organ. This further increases complexity, acquisition time of the data, and costs of the instrument. HAKENBERG ET AL: "THE ESTIMATION OF BLADDER VOLUME BY SONOCYSTOGRAPHY", J Urol, Vol 130, pp 249-251, reported a simple method for calculating bladder volume based on measuring the diameters of the bladder from a cross sectional image taken along the midline sagittal bladder plane only. These diameters give the height and depth of the bladder at the scan plane. The bladder volume is estimated as the product of the height and depth multiplied by an empirically derived constant.

This led to a method used in the current art of performing one or more two-dimensional diagnostic ultrasound 'B' scans to produce images of one or more cross sections through the structure whose volume is of interest, such as the bladder, and then to make several standard reference measurements of that imaged structure which are then inserted into a formula to estimate the cross sectional area or volume as required. For the bladder, transverse and a longitudinal (sagittal) scans are recorded and the height and width of the transverse image and the depth of the longitudinal one are manually measured, then multiplied together to produce a measure of the volume. A scaling constant is usually also included within the calculation which then crudely models the volume of an oblate ellipsoid.

This crude model may have inaccuracies as high as fifty percent. The bladder varies greatly in shape. A single individual's bladder shape will vary according to the degree of filling, most closely approximating the model when significantly full. Between individuals, the shape will vary depending on a number of factors, which may change the actual bladder shape of the apparent shape as shown by an ultrasound scan. The presence or absence of a uterus will change the shape, as will the prostate. Pathology of the bladder, including haematoma, or of the surrounding organs, which may distort the bladder, will also affect the bladder shape.

An ultrasound apparatus for determining the bladder volume is shown in U.S. Pat. No. 4,926,871 to Dipankar Ganguly et al. This discloses a scan head referred to as a sparse linear array with transducers mounted at predetermined angles such that the acoustic "beams" emitted by the transducer tend to a common point. The volume is calculated according to a geometric model. An apparatus is described for automatic calculation of bladder volume from ultrasound measurements in two orthogonal planes. The device is complex, including a stepper motor for deflecting the acoustic "beams". It requires a skilled operator to manipulate the scan head in a particular way to obtain the ultrasound measurements.

Volume measurement based on ultrasound sampling of the bladder with a hand guided transducer mounted in a pantograph has been described by Kruczkowski et al: "A non-invasive ultrasonic system to determine residual bladder volume", IEEE Eng in Medicine & Biology Soc 10TH Ann Conf, pp 1623-1624. The sampling covers the entire bladder, follows a given pattern and is not limited to a single or two cross sections of the bladder. The acquisition procedure is time consuming and thus does not give instantaneous volume measurement results.

Apparatus exist in the prior art whereby the transducer, and thus the beam, are mechanically swept over the volume of the bladder. Such sweeping takes time, meaning that volume measurement is not available instantaneously. Further, no instantaneous feedback on optimal positioning of the apparatus with respect to the bladder is available. In an exemplary apparatus, bladder volume is measured by interrogating a three-dimensional region containing the bladder and then performing image detection on the ultrasound signals returned from the region insonated. The three dimensional scan is achieved by performing twelve planar scans rotated by mechanically sweeping a transducer through a 97 degree arc in steps of 1.9 degrees. The device is thus mechanically complex and requires complex calculations to yield a result.

Ganguly et al in U.S. Pat. No. 5,964,710 entitled "System for estimating bladder volume" disclose a method for determining bladder volume based on bladder wall contour detection from ultrasound data acquired in a plurality of planes which subdivide the bladder. In each single plane of the plurality of planes N transducers are positioned on a line to produce N ultrasound beams to measure at N positions the distance from front to back wall in the selected plan. From this the surface is derived. This procedure is repeated in the other planes as well. The volume is calculated from the weighted sum of the plurality of planes. In Ganguly's method the entire perimeter of the bladder is echographically sampled in 3 dimensions. The equipment required to undertake this sampling in a clinical context is expensive and complex.

All automated methods of determination of an organ volume will encounter the difficulty of dealing with variation in the quality of the scanned image. In a clinical setting it is not practical to always achieve optimum image quality. There may exist a wide range of brightness and contrast conditions in the scan or scans. There will be noise, and the level of this may vary widely.

DISCLOSURE OF THE INVENTION

Clinically, the volume of a patient's bladder may be important. It can be used to determine the residual volume of urine in the bladder following voiding, which may be clinically important. The volume of other organs may also be important. For example the diagnosis of abdominal aortic aneurysm may be made by reference to the volume of the imaged aorta in an ultrasound image.

In one form of this invention although this may not necessarily be the only or indeed the broadest form of this there is proposed a method for determining the volume of a bodily structure including the steps of acquiring at least two ultrasound images, estimating the location of the perimeter of a structure of interest as viewed in cross section in a two dimensional ultrasound image, calculating the cross sectional area of such structures as so viewed, and combining the perimeter and area information from the at least two images to calculate the volume of the structure.

Of particular importance in this method, is the estimate of the location of the perimeter of the structure. In the case of the bladder, this is the perimeter of an area which is fluid filled and hence anechoic. For other structures where the structure of interest is more strongly echoic than the surrounding tissue, the perimeter sought is the perimeter of a highly echoic region.

The varying quality of the ultrasound images, including image noise adds to the difficulty of establishing this perimeter. The nature of the response of tissue to ultrasound also must be accounted for.

A particular problem is differentiation between the well known ultrasound artefact of speckle, and random noise. Random noise will occur in all regions of the image, including those constituting the void which is the structure whose perimeter is to be estimated. Speckle has the appearance of noise, but occurs only in the presence of echoic material, that is organ structure. Thus the presence of speckle means that the speckled area is not part of the void and the edge of the speckled area may define the perimeter being sought. Attempts to filter the image to reduce noise in order to clearly define the void perimeter will usually also reduce speckle, leaving the perimeter no better defined.

A filter which preferentially removes random noise with less effect on speckle will allow a void boundary to be more clearly defined.

Preferably, the process of estimating the location of the perimeter includes the step of applying an anisotropic median filter to the ultrasound data.

The clinical value of the determination of bladder volume is greatly increased if the measurements can be taken as often as desired, without the machine used to make the determination introducing unnecessary practical obstacles. To this end, the device should be as easy and convenient to use as possible.

In preference, the method of performing bladder volume is performed by a handheld ultrasound device, able to be easily and conveniently carried by a clinician.

In preference, the handheld ultrasound device has a weight of less than 500 grams.

Power consumption also contributes to portability. Lower power consumption means that a device can be battery powered and less reliant on frequent recharging.

In preference, the handheld ultrasound device is battery powered, with a power consumption of less than 10 milli-Watts.

BEST MODE FOR CARRYING OUT THE INVENTION

Figure 2:
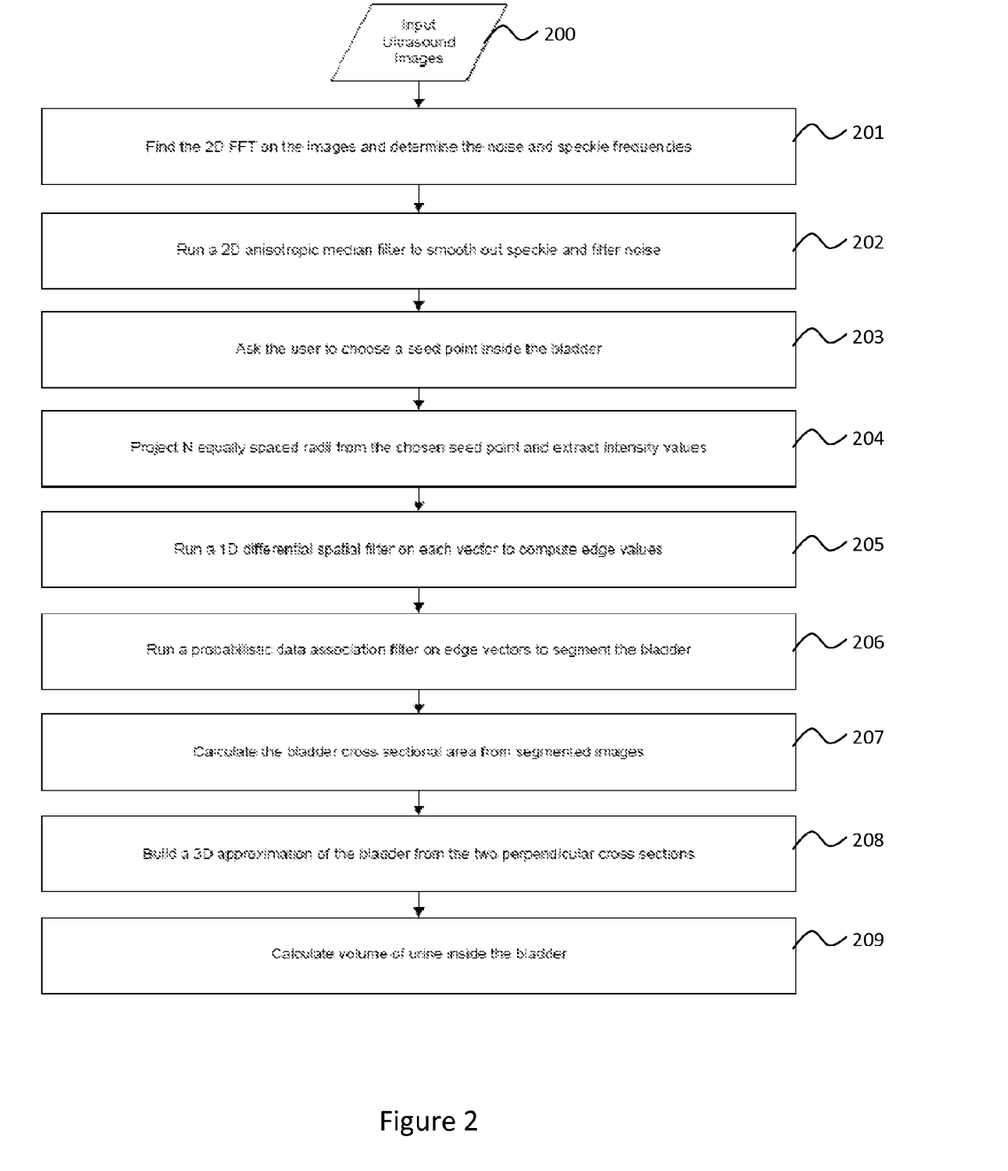
FIG. 2 is a flow chart of the steps of a preferred embodiment of the invention.

Now referring to the illustrations and in particular to FIG. 2, there is shown a flow chart of the method of the invention. The method illustrated is a method for determining the volume of a bladder. However, the method can be used for determining the volume of any organ or body structure which will show a reasonably distinct perimeter in an ultrasound scan. This may include the abdominal aorta, the prostate or other organs.

The first step 200 requires the input of ultrasound images. Preferably, these are two or more cross sectional images of the bladder, taken in directions substantially orthogonal to each other.

These images may be produced by any convenient means, however it is useful for these to be made by an inexpensive hand held ultrasound machine. This greatly expands the usefulness of the determination of bladder volume, since such a machine may available in contexts such as nursing home use, or visiting medical staff use where a full size machine cannot economically be provided.

Figure 1:
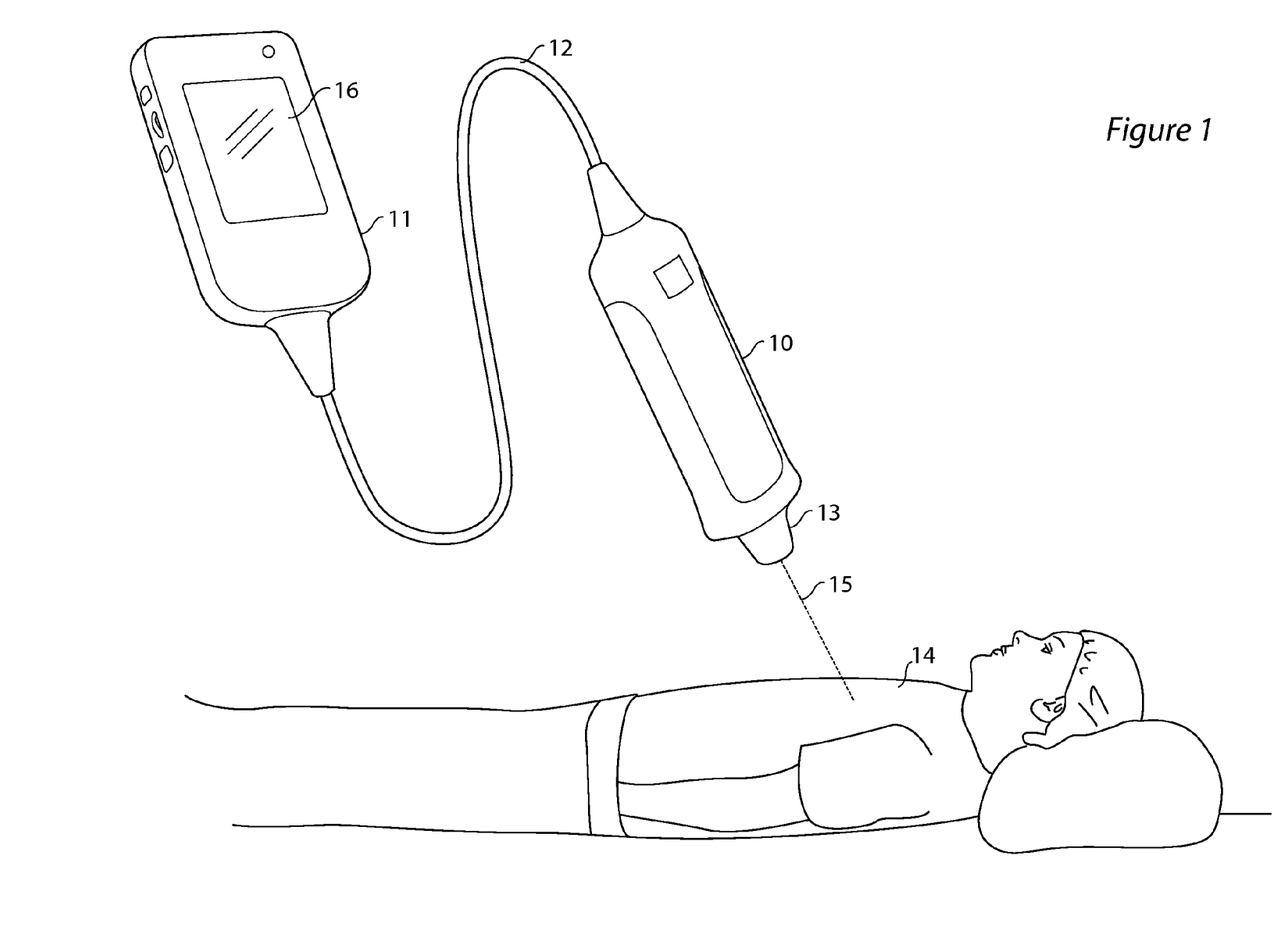
FIG. 1 is a handheld ultrasound device adapted to implement the method of the invention.

A useful machine is illustrated in FIG. 1. There is shown a hand held ultrasound scan device with an ultrasonic probe unit 10, a display and processing unit (DPU) 11 with a display screen 16 and a cable 12 connecting the probe unit to the DPU 11. The ultrasound device has a weight of less than 500 grams. For enhanced portability, it is battery powered, with a power consumption of less than 10 mW.

The probe unit 10 includes an ultrasonic transducer 13 adapted to transmit pulsed ultrasonic signals into a target body 14 and to receive returned echoes from the target body 14.

In this embodiment, the transducer is adapted to transmit and receive in only a single direction at a fixed orientation to the probe unit, producing data for a single scanline 15.

The probe unit further includes an orientation sensor capable of sensing orientation or relative orientation about one or more axes of the probe unit. Thus, in general, the sensor is able to sense rotation about any or all of the axes of the probe unit.

The sensor may be implemented in any convenient form. In an embodiment the sensor consists of a single gyroscope providing information about rotation about only a single axis.

Figure 3:
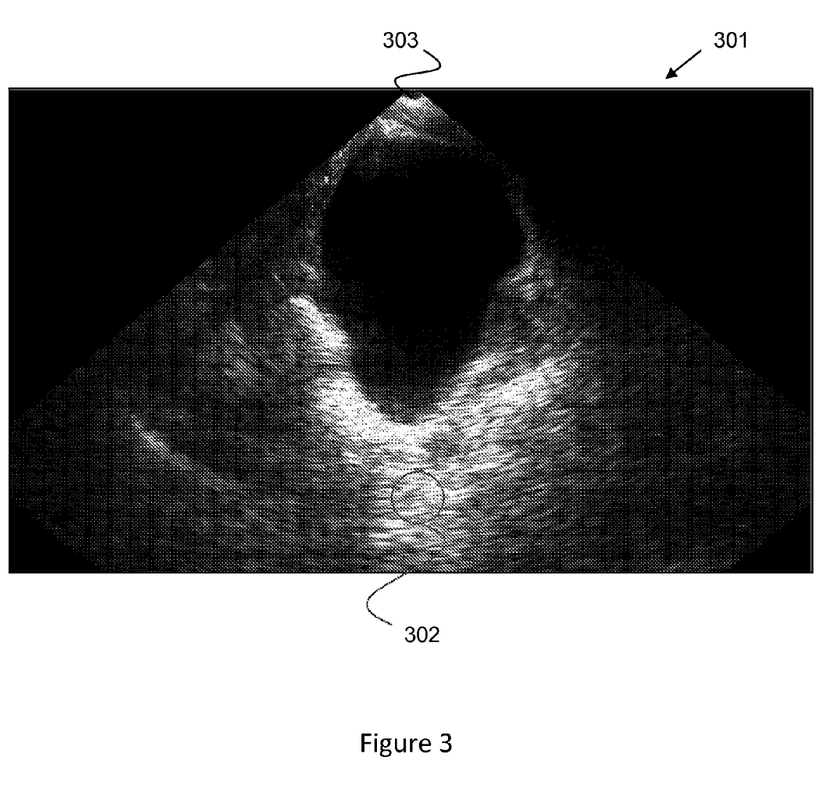
FIG. 3 shows an ultrasound image of a saggital cross section of a bladder.

In order to make the images the bladder is approximately located, and the probe unit 10 positioned at the estimated position of the widest part of the bladder. The unit is then moved to sweep the scanline 15 through a cross section of the bladder to obtain an image. The probe unit is then turned ninety degrees and a further image is made. The images are then processed in the same way in parallel. An example of one image of a pair, a saggital cross section of a bladder is shown in FIG. 3. This image is a standard B mode image, being a sector of a circle with an origin 303.

The bladder shows as an anechoic region 301 with a perimeter defined by reflections from surrounding organs. The reflections show the classic "speckled" appearance which is the artifactual noise called speckle. Any reflectors within the bladder void are random noise.

The image in now filtered to filter out noise, smooth speckle beyond the bladder edge and preserve the bladder boundary.

In the second step 201 of the method a 2D fast Fourier transform (FFT) is computed on the ultrasound image to determine the noise and speckle patterns This gives the result that the frequency components in the noise section of the image are randomly distributed while more high frequency harmonics are needed to reconstruct the image along a scanline in speckle regions. Thus the speckle in not purely random noise. There is a regular characteristic to the speckle. This regularity is found to be related to the direction of the original scanline used to capture the scanned image.

Figure 4:
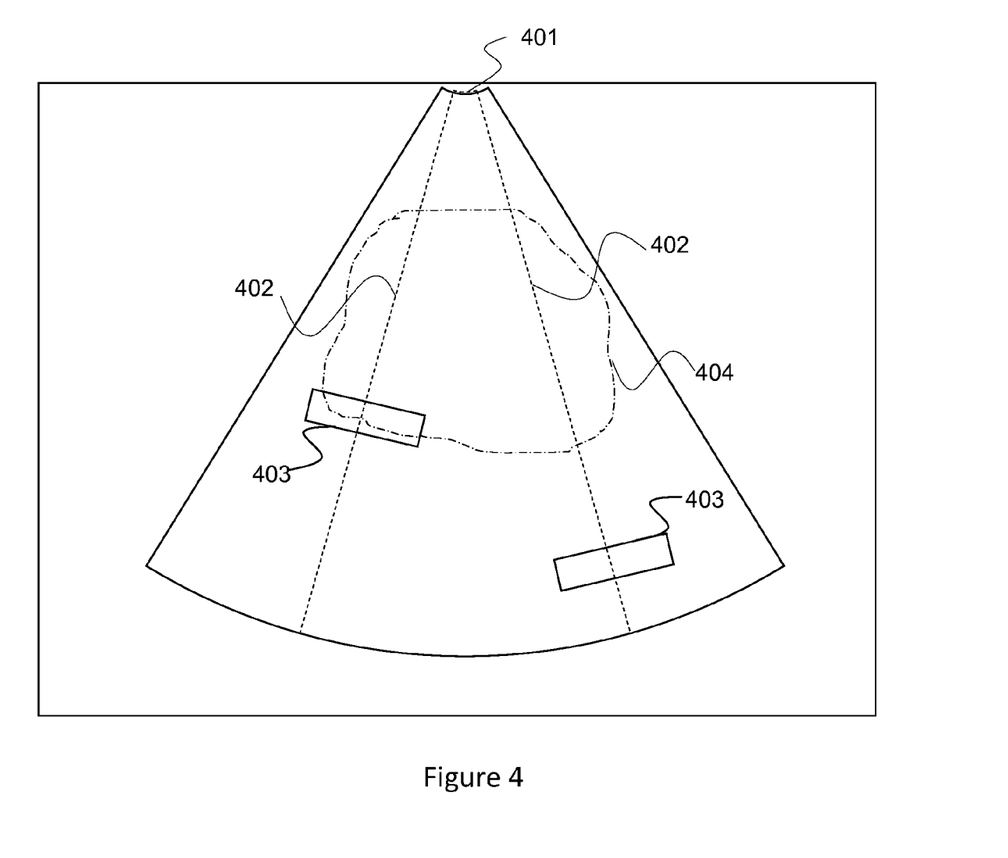
FIG. 4 shows a diagrammatic representation of the application of the anisotropic filter of the invention.

This information is then used to design an anisotropic median filter, shown diagrammatically in FIG. 4. FIG. 4 shows an ultrasound image to which the steps of the method are applied. It is a sector of a circle, with a source point 401. The scan is made up of a series of scan lines 402. The scan shows the outline of an organ, in this case a bladder, 404.

In a third step 202, an anisotropic median filter is applied to the image data. A filter mask 403 is used which is a rectangle that is wider perpendicular to the scan line 402. The scan line for any image may be recreated as a line between any data point in the image and the source point 401.

This has the effect of filtering out noise more than filtering out speckle due to the speckle being arranged in bands that are perpendicular to the scan line.

This step need not be undertaken in each case. The values for the anisotropic filter which will be close to optimum for the range of images likely to be useful in a clinical context may be pre-calculated and this filter employed for all images.

Figure 5:
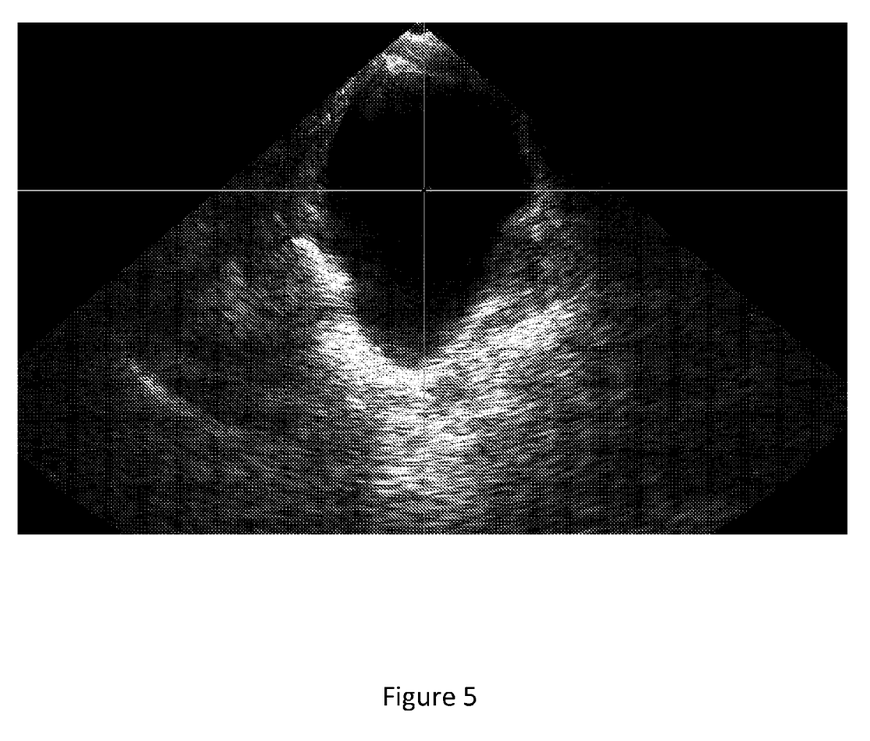
FIG. 5 shows the selection of a seed point for the method of the invention.

In order to define the perimeter of the bladder, it is necessary to establish a point which is definitely inside the perimeter. This may be done in a variety of ways, but the simplest step 203 is to have a user identify a point within the bladder. This can be done by the user touching a point within the displayed image on a touchscreen display, or by manipulation of cross hairs as shown in FIG. 5 but any convenient method may be used.

Figure 6:
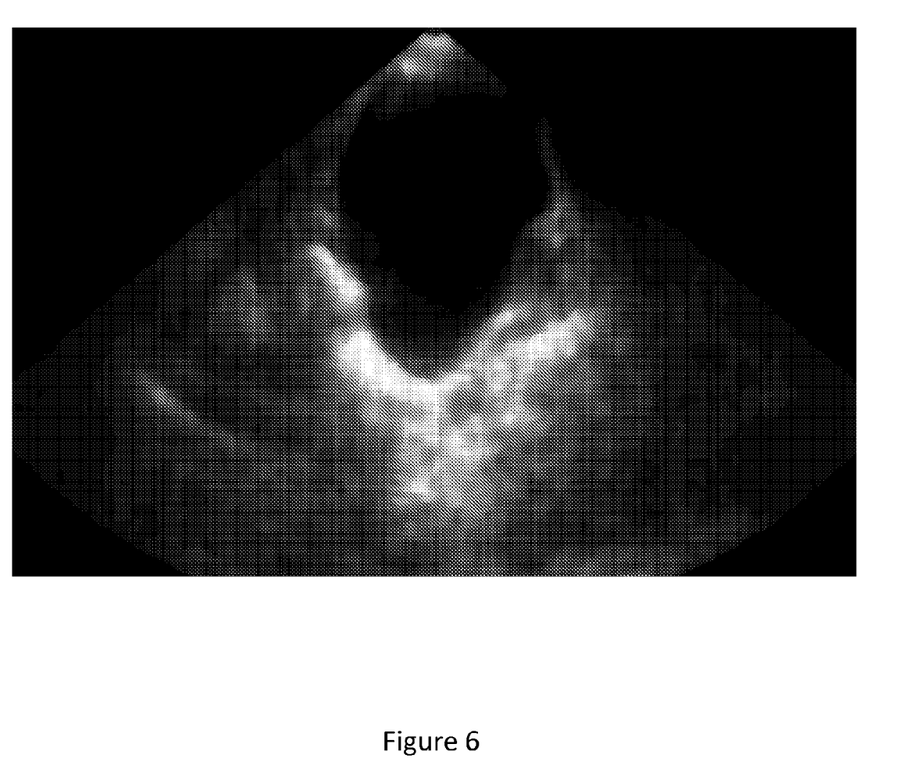
FIG. 6 shows the result of the application of an anisotropic median filter to the image of FIG. 3.
Figure 7:
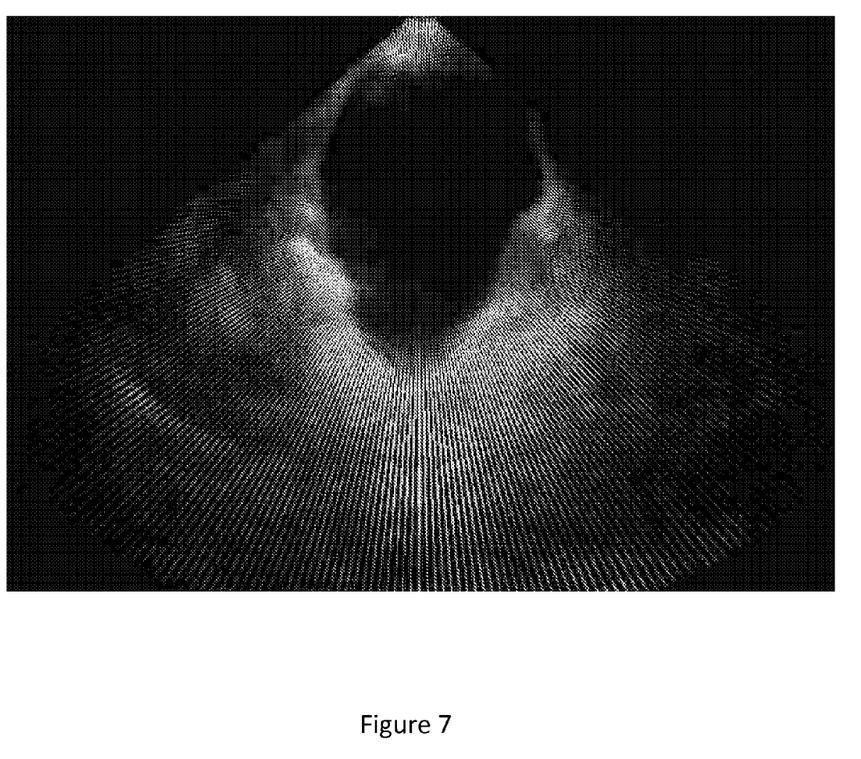
FIG. 7 shows N equally spaced radii projected from a seed point for the method of the invention.

The result of the application of an anisotropic median filter to the image of FIG. 3 is shown in FIG. 6. This is now used to locate the perimeter of the bladder. The selected seed location is transferred to this image. N equally spaced radii are projected from the seed point as shown in FIG. 7, and the pixel intensities along each radius are extracted and stored. An edge detector filter is applied along each radius.

This edge detector filter is a differential spatial filter used to calculate the edge value along each radius as shown in the equation below.

$$E(r)=(1-I(r))^4\{I(r+3\Delta r)+I(r+2\Delta r)+I(r+\Delta r)+I(r)-I(r-\Delta r)-I(r-2\Delta r)-I(r-3\Delta r)\}$$

Where E is the edge value, I is the pixel grey level value, and r is the distance from the seed point.

In this application, only the transition from dark regions to bright regions are significant since the edge detection algorithm starts from a point within the bladder area and it is known that the bladder is the darkest region within the image, hence only positive edge value are used in the algorithm.

Further, this means that transitions of brightness from very dark (anechoic) regions to lighter (echoic) regions, are more likely to be part of the perimeter than transitions of brightness of the same magnitude where the transition is from an area of some echo to an area of greater echo. The latter type of transition is much more likely to be speckle.

Accordingly, as can be seen in the above equation, the edge detection filter includes a $(1-I(r))^4$ term. Where the grey level of the pixel is low, meaning the pixel is in a substantially anechoic region, this term will be close to 1. As the grey level increases, it will fall rapidly toward zero. This term therefore applies a heavy weighting to transitions starting from a very dark pixel, increasing the likelihood that these will be seen as part of the perimeter of the bladder.

In embodiments where the perimeter of a structure which is not so highly anechoic is being defined, the order of this term is reduced.

In embodiments where the structure being outlined is highly echoic and the background less echoic, the sign of the weighting is reversed, the term becoming $I(r)^4$. Again, where the structure being outlined is less highly echoic, the order of the term is reduced.

Figure 8:
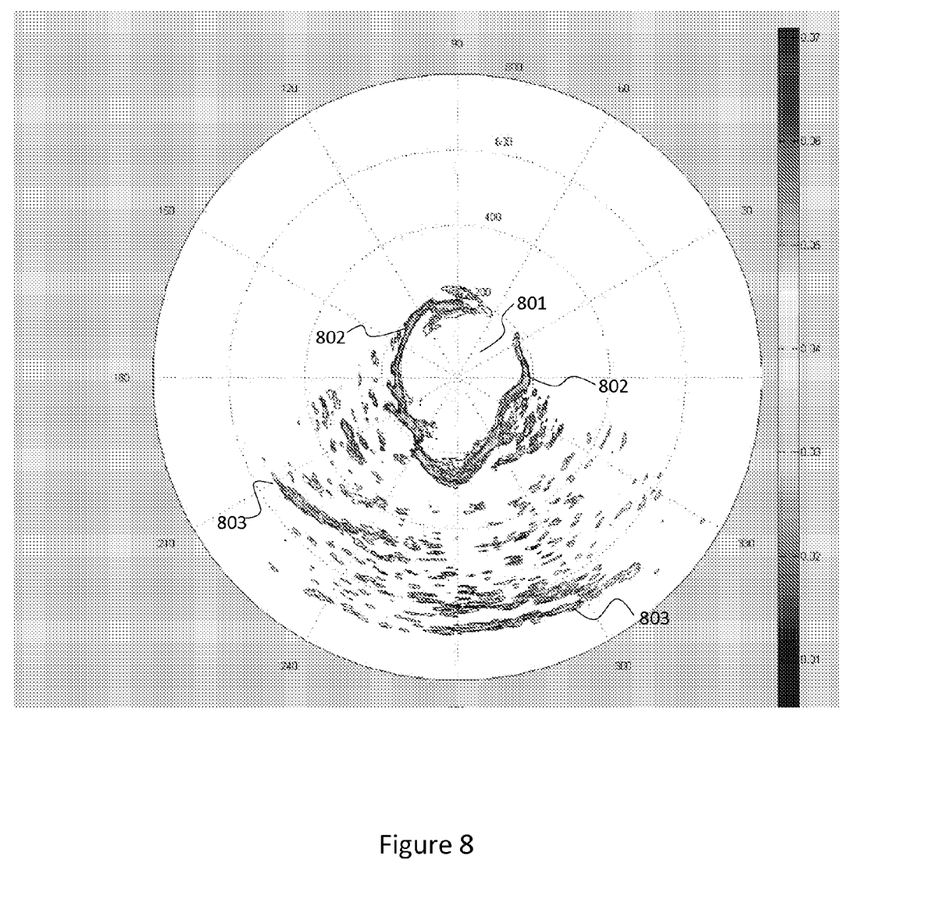
FIG. 8 shows the image resulting from the application of an edge detection filter to the image of FIG. 3.

The image resulting from the application of this filter to the image of FIG. 3 is shown in FIG. 8. It can be seen that there now exists a clearly visible anechoic area 801 which is substantially free of noise. The area 801 is surrounded by a reasonably clearly delineated echo producing perimeter 802. There are also other echo producing areas 803 which are not part of the perimeter of the bladder region.

The perimeter of the bladder is now able to be defined. This s described as segmenting the bladder image. This is done by applying probabilistic data association filter (PDAF) to the results of the edge detection step.

Figure 9:
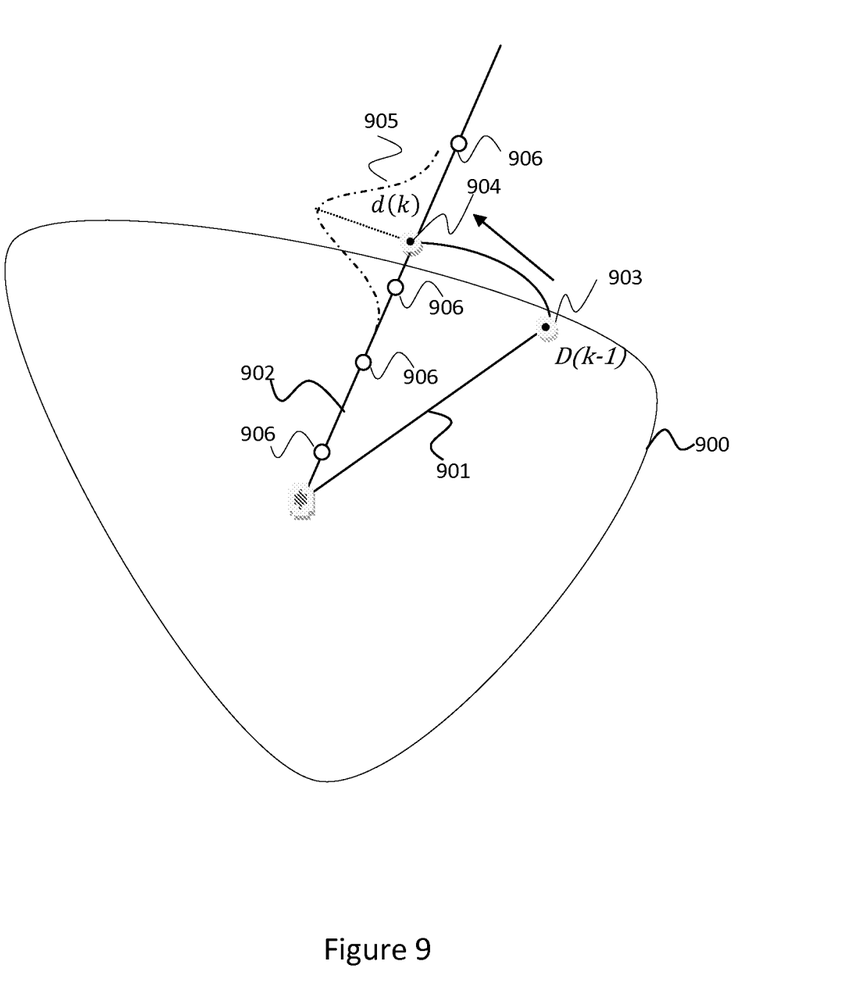
FIG. 9 is a diagrammatic representation of the operation of the PDAF of the invention.

The basic operation of the PDAF is shown FIG. 9. There is the true bladder wall contour 900, which is the actual, physical bladder wall. The location of this wall is unknown. There are two of the N radii 901,902 projected at step 5 of the method 205. An estimate of the distance d(k) 904 of the bladder wall 900 from the seed point 907 along the $k^{th}$ radius is made. The initial estimate is based on a "model" of the bladder which assumes that it is a circle centred on the seed point, hence the initial estimate is that the distance along each radius to the bladder wall is constant. Hence:

$$d(k)=D(k-1)$$

where D(k−1) 903 is the true value of the distance along the $k-1^{th}$ radius to the bladder wall.

Each point $r_i$ 906 along the radius is assessed for inclusion on the boundary. This is done using a formula which weights the likelihood of the point being on the boundary by both the magnitude of the edge E(r) and by its proximity to the model estimated boundary position d(k) 904. The proximity weighting is made by applying a weighting curve 905 which is a normal distribution with a mean d(k). The output of this step is a measurement estimate of the boundary radius Z(k).

A Kalman filter is then applied which weights the model estimate d(k) against the measurement estimate Z(k).

The output of this is an estimate for the value of the distance D(k) from the seed value to the true bladder wall.

The algorithm is applied sequentially to each radius sweeping around the perimeter twice to ensure that the perimeter estimate converges to a closed shape.

Figure 10:
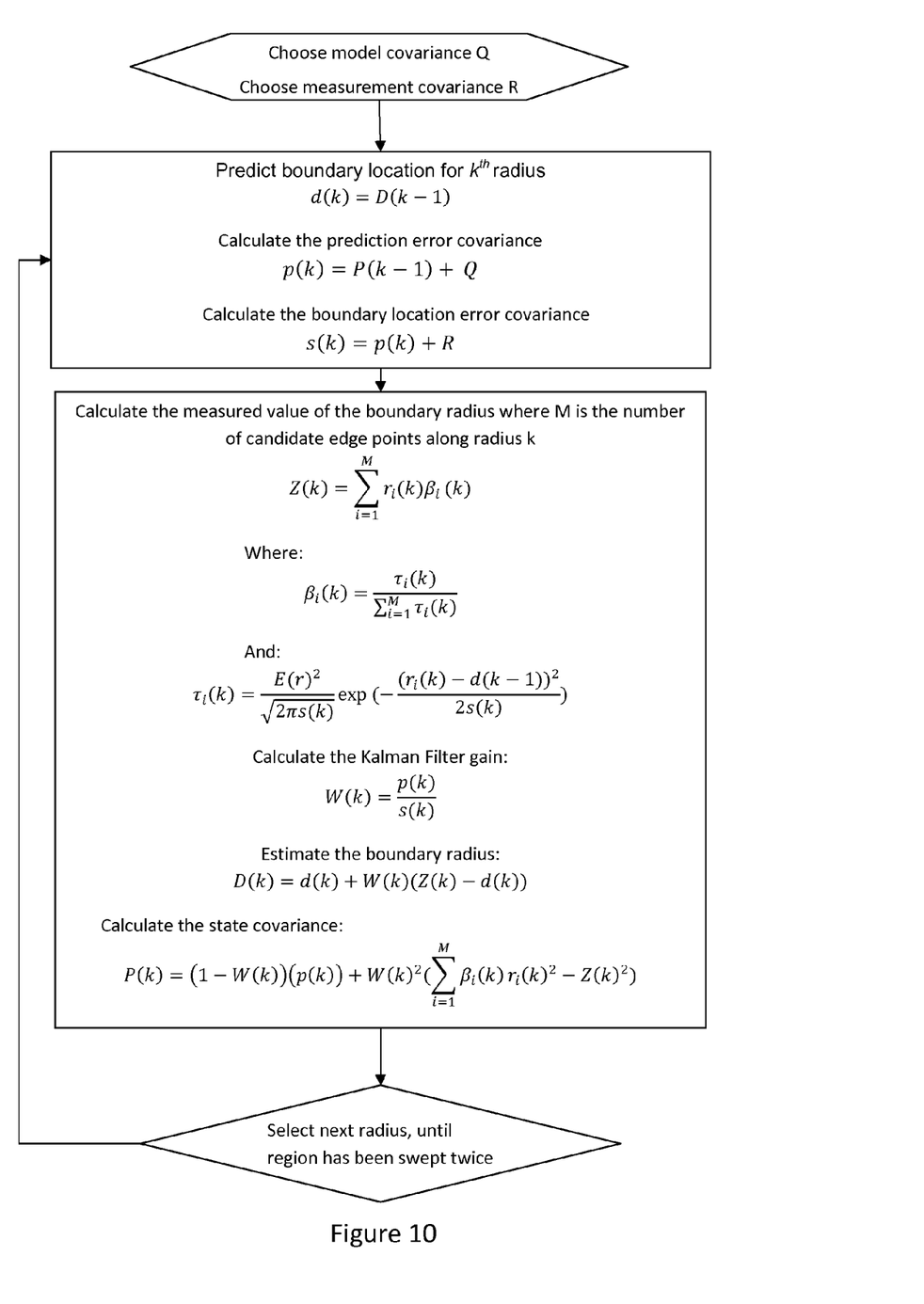
FIG. 10 is a flow diagram of the steps of the PDAF of the invention.

FIG. 10 shows the algorithm steps of the PDAF in greater mathematical detail.

The algorithm has proved to be very robust in segmenting the bladder contour in bladders of different shapes and sizes. Furthermore, the algorithm is able to accurately approximate the wall trajectory in the case of very large shadowing.

Figure 11:
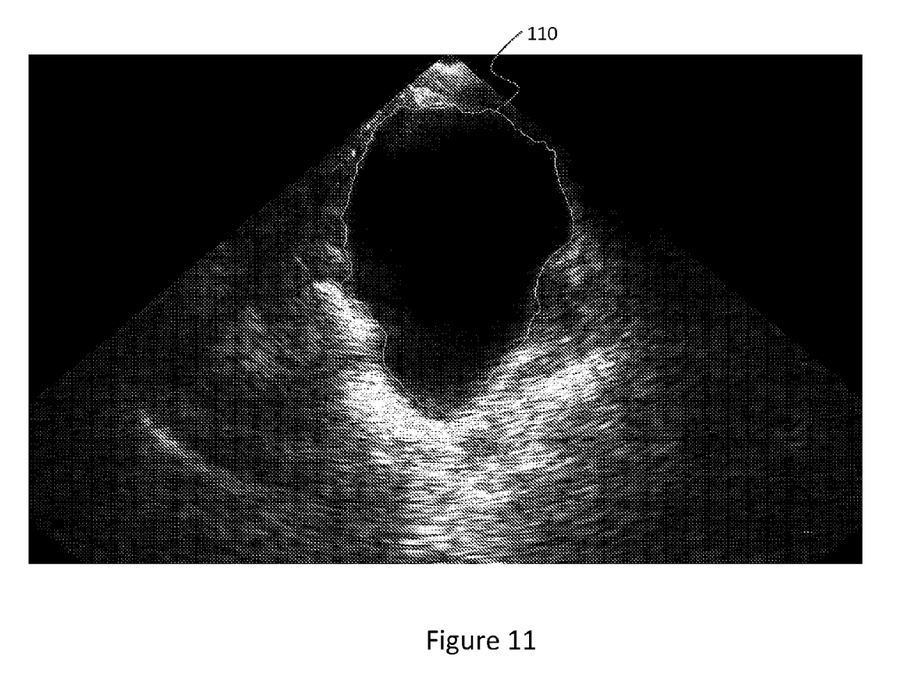
FIG. 11 shows the bladder wall of the image of FIG. 3 delineated by perimeter line.

FIG. 11 shows the bladder wall of the image of FIG. 3 delineated by perimeter line 110.

Bladder shape and position can drastically vary with age, gender, filling degree and disease. In the adult patient the empty bladder has the shape. The bladder shape is complex and cannot be represented by a single geometrical formula such as ellipsoid, sphere etc. This explains the large error that several studies obtained when a single geometric model was used.

In a preferred embodiment, two bladder perimeters calculated from the images created in the saggital and transverse direction are calculated and used to calculate the bladder volume.

The cross sectional area of the bladder as shown in each of these images may be calculated by dividing the bladder into triangular elements made by the equally spaced radii from the seed points. This gives a series of triangles with vertices a, b, c of the type shown in FIG. 12.

Figure 12:
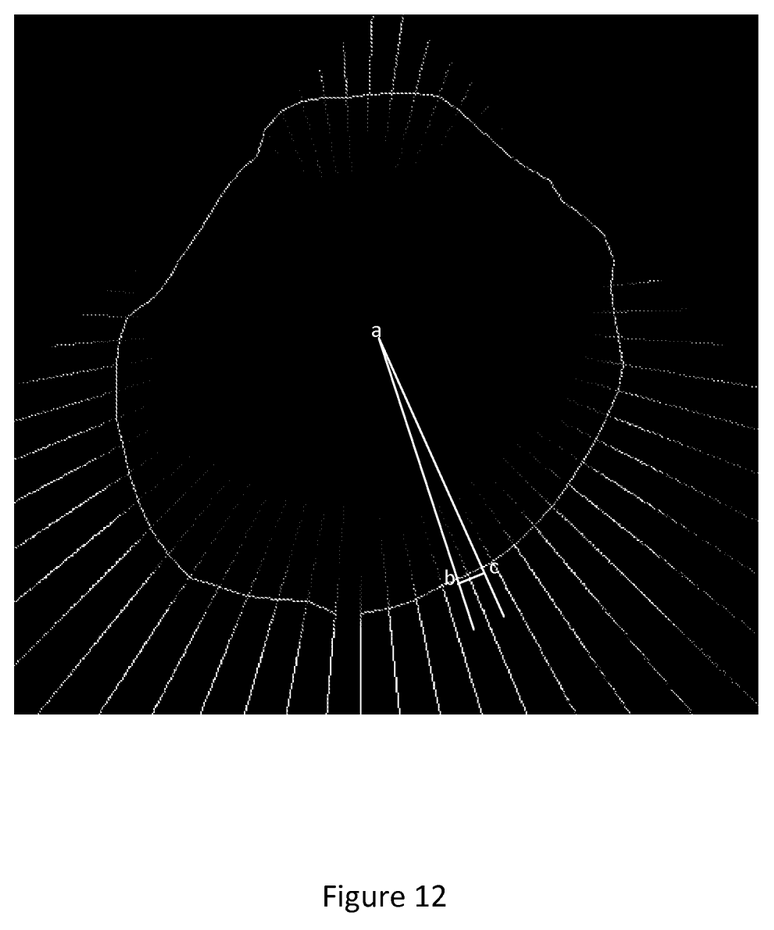
FIG. 12 shows a diagrammatic representation of the determination of the area of a cross section of a bladder image.

The area A of each triangle may be calculated using:

$$A = \frac{1}{2} \det \begin{pmatrix} x_a & x_b & x_c \\ y_a & y_b & y_c \\ 1 & 1 & 1 \end{pmatrix}$$

Summing the areas of each of the series of triangles will give the area of the cross section of the bladder.

The volume may then be calculated from the areas. One way of doing so is to use the following equation to determine the bladder volume V:

$$V = \alpha \beta H_{saggital} D_{saggital} W_{transverse}$$

Where:

$$\alpha = \frac{A_{saggital}}{H_{saggital} D_{saggital}}$$

$$\beta = \frac{A_{transverse}}{W_{transverse} D_{transverse}}$$

Hence:

$$V = \frac{A_{saggital} A_{transverse}}{D_{transverse}}$$

In further embodiments, areas of the image which are definitely part of the bladder or definitely not part of the bladder may be separately identified. This may be done by any means, including direct user classification. Preferably, automated methods are used, such as filters which detect the characteristic streaky appearance of prostate tissue. The calculated parameter is checked to ensure that explicitly classified areas fall correctly within or outside of the bladder perimeter, and the perimeter adjusted if necessary.

In a further embodiment, the single scanline probe unit of FIG. 1 is replaced by a probe unit capable of producing a B mode scan without user movement of the probe unit. The probe unit may include a linear or curvilinear array transducer or a phased array transducer. It may include a mechanically moved transducer.

The probe unit also includes an orientation sensor, which may be a gyroscope. In use, either a transverse or saggital cross sectional image of the bladder is taken, preferably across the widest portion of the bladder. The face of the probe unit is then maintained in this position, while the probe unit is moved by the user through an arc approximately at right angles to the plane of the first acquired image. Images are taken whilst the probe is being moved, to give a series of 2D slices through the bladder.

Data from the gyroscope is used to track the relative positions of these slices. The location of the perimeter and the cross sectional area of the bladder are then determined in the 2D slices using the methods disclosed herein, while trilinear interpolation techniques are used to perform 3D scan conversion and estimate the volume of the bladder from the 2D slices.

Although the invention has been herein shown and described in what is conceived to be the most practical and preferred embodiment, it is recognised that departures can be made within the scope of the invention, which is not to be limited to the details described herein but is to be accorded the full scope of the appended claims so as to embrace any and all equivalent devices and apparatus.

The invention claimed is:

1. A method for determining the volume of a fluid filled bodily structure including the steps of:
    a. acquiring image data for at least two ultrasound images of the bodily structure, each of the ultrasound images including speckle artifacts and random noise;
    b. applying an anisotropic median filter to the image data of each of the ultrasound images to generate and display a corresponding filtered image for each of the ultrasound images, wherein the anisotropic median filter:
        (1) uses a filter window defined by a rectangle which is wider in a direction perpendicular to the approximate path of a scanline which produced the area of the image being filtered relative to the width of the rectangle in a direction parallel to the approximate path of the scanline, and
        (2) is configured to reduce, in each of the filtered images, display artifacts due to the random noise to a greater extent than the speckle artifacts to form, in each filtered image, an image delineation of a perimeter of the bodily structure, the image delineation including a pattern of speckle artifacts preserved in each filtered image;
    c. estimating, using the image delineation in each displayed filtered image, the location of the perimeter of the bodily structure as viewed in cross section in each filtered ultrasound image;
    d. calculating, from each displayed filtered image, the cross sectional area of the bodily structure as so viewed using the estimated perimeter location; and e. combining the perimeter and area information calculated from the displayed filtered images to calculate the volume of the bodily structure.

2. The method of claim 1 wherein a fast Fourier transform is applied to the image data of each of the ultrasound images to determine parameters of said anisotropic median filter.

3. The method of claim 1 wherein the bodily structure is a bladder.

4. The method of claim 1 wherein the bodily structure is an aorta, measured in the region of the abdomen.

5. The method of claim 1 wherein estimating, from each displayed filtered image, the location of the perimeter of the bodily structure as viewed in cross section in each filtered ultrasound image, includes the steps of:
  a. selecting a seed point located within an area bounded by the image delineation;
  b. projecting N equally spaced radii from the selected seed point to intersect the image delineation;
  c. processing pixel intensities along each radius to determine for each point along a respective radius a magnitude of an edge value;
  d. applying a geometric model of the bodily structure to estimate, for each radius, the location of an intersection point of the radius and the perimeter; and
  e. applying, for each point along each radius, a weighting function to estimate a value of a distance of the perimeter from the seed point based on the magnitude of the edge value and a proximity to the corresponding estimated location of the intersection point.

6. The method of claim 5 wherein the step of processing pixel intensities along each radius includes applying an edge detection filter along each radius.

7. The method of claim 6 wherein the edge detection filter includes a differential spatial filter.

8. The method of claim 7 wherein the differential spatial filter is expressed by the form:

$$E(r)=(1-I(r))^4\{I(r+3\Delta r)+I(r+2\Delta r)+I(r+\Delta r)+I(r)-I(r-\Delta r)-I(r-2\Delta r)-I(r-3\Delta r)\}$$

where E is the edge value, I is a pixel grey level value, and r is a distance from the seed point.

9. A hand held portable ultrasound apparatus including:
a. an ultrasound transducer;
b. control electronics for controlling the transducer to transmit pulsed ultrasonic signals into a target body and to receive returned echoes from the target body;
c. image acquisition electronics to produce, from returned echoes, image data for at least two ultrasound images; and
d. a processor configured to:
  (1) apply an anisotropic median filter able to act on the image data of each of the ultrasound images, the images including speckle artifacts and random noise, to generate and display a corresponding filtered image for each of the ultrasound images, wherein the anisotropic median filter:
    (i.) uses a filter window including a rectangle which is wider perpendicular to the approximate path of a scanline which produced the area of the image being filtered relative to the width of the rectangle in a direction parallel to the approximate path of the scanline, and
    (ii.) reduces, in each of the filtered images, display artifacts due to the random noise to a greater extent than the speckle artifacts to form, in each filtered image, an image delineation of a perimeter of the bodily structure, the image delineation having a pattern of speckle artifacts preserved in each filtered image;
  (2) determine, from each displayed filtered image, the location of the perimeter of the bodily structure as viewed in cross section; and
  (3) calculate the values of the perimeter and the area of the bodily structure as shown in each of the displayed filtered images to calculate from these values a volume of the bodily structure, and
  (4) display the calculated volume to a user.

* * * * *